United States Patent [19]
LaBombard

[11] Patent Number: 5,309,906
[45] Date of Patent: May 10, 1994

[54] ENDOBRONCHIAL TUBE ASSEMBLY

[75] Inventor: Denis LaBombard, Georgetown, Mass.

[73] Assignee: Smiths Industries Medical Systems, Inc., United Kingdom

[21] Appl. No.: 967,631

[22] Filed: Oct. 28, 1992

[51] Int. Cl.⁵ .......................................... A61M 16/00
[52] U.S. Cl. .............................. 128/207.14; 128/911; 128/912; 604/280
[58] Field of Search ............... 604/280; 128/207.14, 128/207.15, 911, 912, DIG. 26

[56] References Cited

U.S. PATENT DOCUMENTS

| | | | |
|---|---|---|---|
| 3,890,976 | 6/1975 | Bazell | 128/207.15 |
| 4,140,119 | 2/1979 | Pollack | 604/208 X |
| 4,233,984 | 11/1980 | Walling | 128/207.14 |
| 4,351,328 | 9/1982 | Bodai | 128/912 X |
| 4,489,721 | 12/1984 | Ozaki | 128/205.24 |
| 4,506,665 | 3/1985 | Andrews | 128/202.27 |
| 4,557,261 | 12/1985 | Rügheimer | 128/202.27 |
| 4,598,706 | 7/1986 | Darowski et al. | 128/205.24 |
| 4,670,009 | 6/1987 | Bullock | 604/280 |
| 4,953,547 | 9/1990 | Poole | 128/203.12 |
| 5,188,593 | 2/1993 | Martin | 604/43 |

FOREIGN PATENT DOCUMENTS 1621945  1/1991  U.S.S.R. ................. 128/912

Primary Examiner—Edgar S. Burr
Assistant Examiner—Eric P. Raciti
Attorney, Agent, or Firm—Pollock, Vande Sande & Priddy

[57] ABSTRACT

A respiratory intubating device for carrying a gas to or from the lungs of a patient including a flexible tubular member having a pair of parallel lumens for extending from a proximal area at the patient's mouth to a distal area at a bronchus of the patient, and an adapter integrally connected to the tubular member for interconnecting the tubular member with a source of gas and for providing access for surgical instruments. The adapter includes a Y-shaped member having a pair of hollow branches which lead to the pair of lumens of the tubular member and a pair of hollow stem members integrally connected to the hollow branch members at about a right angle thereto, and extending upwardly to aim across the patient's face. The Y-shaped member including the junctions of the branch members and the stem members are encased in a soft flexible plastic.

5 Claims, 2 Drawing Sheets

ENDOBRONCHIAL TUBE ASSEMBLY

The present invention relates to respiratory intubating devices for introducing a gas into the lungs of a patient.

BACKGROUND OF THE INVENTION

Devices for introducing gases, such as air or an anesthetizing gas, into the lungs of a patient are well-known. Such devices typically comprise a flexible tubular member having a pair of conduits extending from a proximal end portion at a patient's mouth for connection to a source of gas such as a breathing circuit to a distal end portion in a patient's bronchus region. An orifice is provided at the distal end portion of each conduit for introducing gas into the lungs. The distal end portion of these devices is also typically provided with means, such as inflatable cuffs, for blocking flow of gas along the outer surface of the tubular member.

While these devices have proved to be useful, further developments and improvements are desirable, especially at the proximal end portion of the device. Problems may arise in this area when flexible hoses leading to the intubation device from a source of gas interfere with a surgical site, or when means are not provided for securing the device in the desired position within the patient's respiratory system.

SUMMARY OF THE INVENTION

In accordance with the present invention, there is provided a surgical device for conducting a gas, such as air or an anesthetic, to and from the lungs of a patient. The device comprises an elongated flexible tubular member adapted to extend within the patient's respiratory system from a proximal end portion at the patient's mouth to a pair of orifices at a distal end portion, one at the trachea and the other in a bronchus. The tubular member comprises first and second parallel lumens for conducting a gas from the proximal to the distal end portion, and is provided with seal means, such as inflatable cuffs, for directing gas into a desired region of the lungs and for preventing gas from passing along the tube between its outer surface and the respiratory tract.

The device includes an adapter member formed integrally with the flexible tubular member at its proximal end for interconnecting the parallel lumens with suction means and with a source of gas. The adapter member comprises a Y-shaped member having first and second hollow branch portions which converge to meet the first and second lumens and, with the first and second lumens, form first and second gas passages which extend between the hollow branch portions and the orifices at the distal end portion of the flexible tubular member. A pair of hollow stem members are fixed at an angle of about 90° to the hollow branch portions of the Y-shaped member and are in fluid communication with the hollow branch portions. Connection means are provided for introducing gas from a gas source into the hollow stem members.

The device also includes a flexible plastic member which encases the Y-shaped member and the junction of the Y-shaped member and the hollow stem members. This plastic encasement functions as a bite block for immobilizing the proximal end portion of the flexible tubular member and for preventing its longitudinal movement within the respiratory system of the patient. In addition, the plastic member reinforces the 90° connection between the hollow stem members and the hollow branch members and ensures an adequate seal at the juncture of these members. The present invention provides a compact assembly at the junction of suction and ventilating tubing and by orienting ventilating hoses so that they are directed to pass across the patient's head, remove them from surgical areas which involve the lungs or trachea.

DETAILED DESCRIPTION OF THE INVENTION

The present invention may be incorporated in an endobronchial tube assembly, the distal end of which is adapted to extend into the bronchus of either lung.

Figures 1, 2:
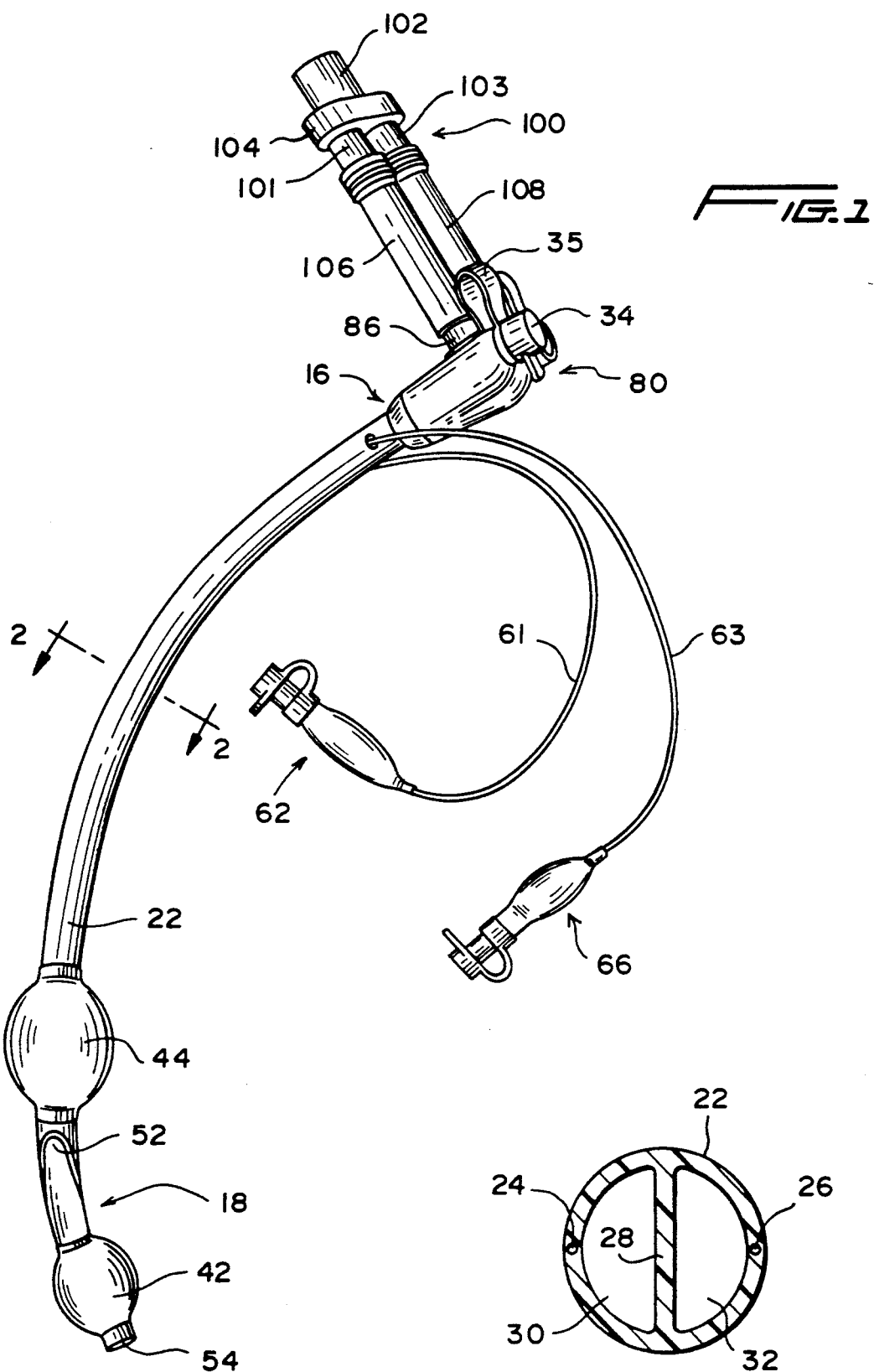
FIG. 1 is a side view partially in perspective of an endobronchial tube assembly in accordance with a preferred embodiment of the present invention.
FIG. 2 is a sectional view of the tube of FIG. 1.
Figure 3:
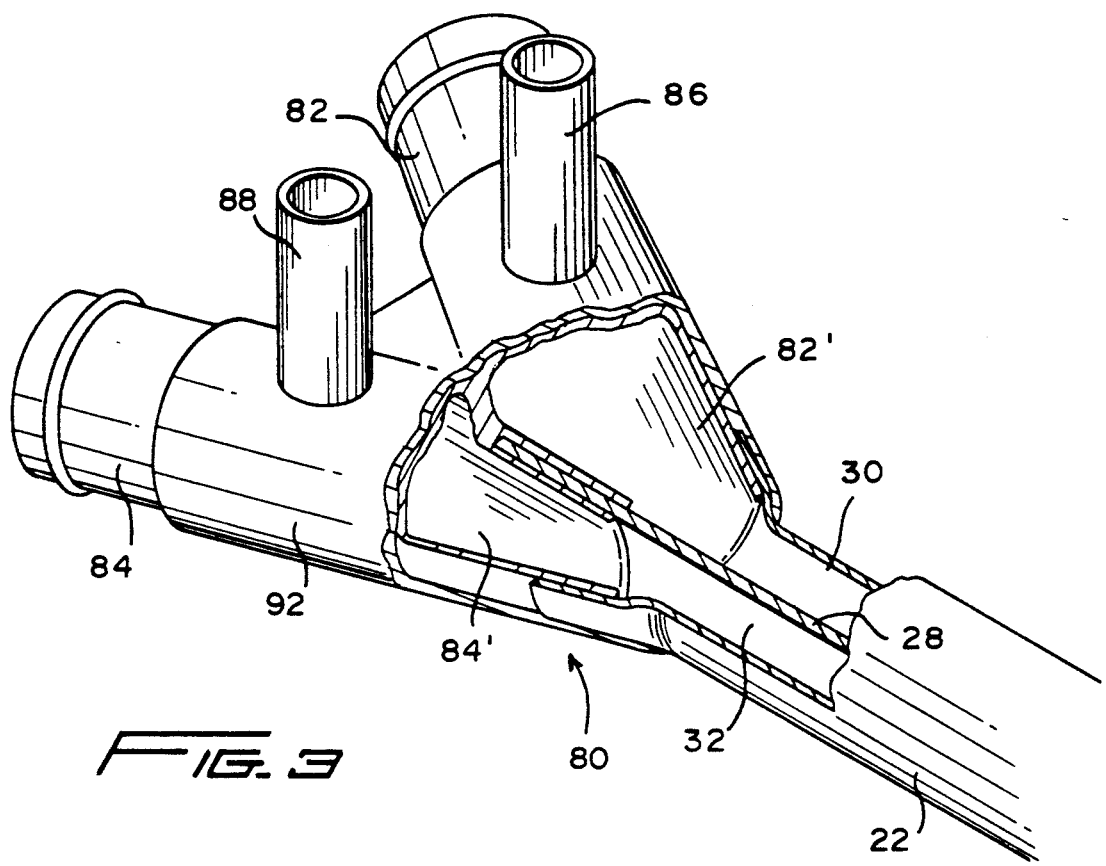
FIG. 3 is an isometric view, partly in section, of the proximal end portion of the present invention.
Figure 4:
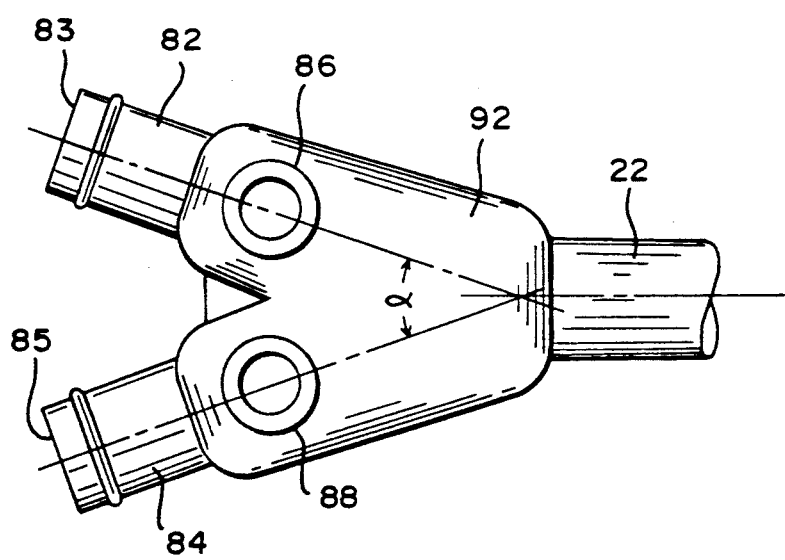
FIG. 4 is a top view of an embodiment of the Y-shaped member showing the flexible plastic member encasing the junctions.

Referring to FIG. 1, a preferred embodiment of an endobronchial tube assembly 10 incorporating the present invention comprises an elongated, flexible, tubular member 22 having a proximal end portion 16 for positioning at a patient's mouth and a distal end portion 18 for positioning at a bronchus of the patient. As shown in FIG. 2, a septum 28 divides tubular member 22 into a pair of D-shaped, longitudinally-extending lumens 30, 32. Tubular member 22 is preferably circular in cross-section as shown in FIG. 2 and its size is variable, depending on the size of the patient undergoing surgery. The tube is preferably formed from polyvinyl chloride by techniques well-known in the art.

A flexible bronchial cuff 42, which is inflatable through pilot balloon inflation indicator 62, a tube 61 and a passage 24, engages the interior walls of the bronchus (not shown), thus isolating the left and right lungs from each other. In a like manner, a tracheal cuff 44, which is inflatable through pilot balloon inflation indicator 66, tube 63 and passage 26, engages the interior walls of the trachea (not shown) to isolate both lungs from the atmosphere. Passages 24, 26 are formed in the walls of tubular member 22 to provide fluid communication from tubes 61, 63 to cuffs 42, 44. Conventional valve members (not shown) are provided with pilot balloon inflation indicators 62, 64 to maintain the cuffs inflated as necessary.

Distal end portion 18 of tube 22 ends in an orifice 54 for introducing a gas into one lung. An orifice 52 is provided in a side wall of tubular member 22 between cuffs 42 and 44 for introducing a gas into the other lung.

Adapter means 80, which is integrally formed with proximal end portion 16 of tubular member 22, comprises a Y-shaped member having hollow branch members 82 and 84 having passages 82', 84', respectively; hollow stem members 86 and 88 each joined at a substantially right angle to a plane defined by the center lines of hollow branch portions 82 and 84, respectively; and, a flexible soft plastic member 92 encasing the Y-shaped portion and the juncture of hollow stem members 86 and 88 with hollow branch members 82 and 84.

In a preferred embodiment of the present invention, hollow branch members 82 and 84 diverge from each other sufficiently to provide a space between stems 86 and 88. However, the angle formed between branch members 82 and 84 should be small enough to minimize the bend that a stylet or surgical instruments must traverse in passing into and through tube 22. An angle α between about 30° and 40° has been found to be useful in meeting these conditions.

Passages 82' and 84' of hollow branch members 82 and 84 join lumens 30 and 32, respectively, and provide a passage with only a slight bend from ports 83 and 85 into lumens 30, 32. As a result of this virtually straight passage, a stylet can easily be introduced either from port 83 into lumen 30 or from port 85 into lumen 32 for controlling the configuration of tube 22 when introducing the tube into a patient's respiratory passage. Ports 83 and 85 are adapted for introducing instruments for suction and bronchoscopic viewing of the lungs into lumens 30, 32, and are provided with closures, such as a cap 34, shown for port 82 (see FIG. 1) when introducing a gas into the patient's lungs. Cap 34 is secured to adapter means 80 by a plastic strap 35, one end of which is attached around hollow stem member 86.

Hollow stem members 86, 88 are a part of the passage for conducting gas between a source of gas and lumens 30, 32, and are fixedly secured to hollow branch members 82 and 84 at about right angles thereto so as to be directed upwardly in a direction away from a patient's chest area. tubing which connects a source of gas to the endobronchial tube assembly thus crosses a patient's face and avoids the surgical area of the chest.

Plastic member 92 fits closely around branches 82 and 84 of the Y-shaped member and the juncture of these branches with stem members 86, 88, respectively. Plastic member 92 extends sufficiently far in the patient's direction to permit it to serve as a bite block to help retain the assembly in position. In addition, plastic member 92 as an encasement reinforces the connection between branch portions 83, 85 and stem members 86, 88 and may serve as a seal to prevent gas from escaping at a juncture of these members. A plastic such as polyvinyl chloride having a thickness of about 1.5 to about 2 mm and being soft enough to be indented by pressure of teeth on its surface has been found to be useful. A bite block having a hardness from about 60 to about 80 on the Shore A durometer scale is preferred. Plastic member 92 may be formed around the branches 82, 84 and stem members 86, 88 by conventional methods well-known in the art, such as by an insert molding operation.

In a preferred embodiment of the present invention, the endobronchial tube assembly includes a bifurcation connector 100 which comprises a manifold member 104 for connecting a hollow stem member 102 with tubular members 101 and 103. Hollow stem member 102 is adapted for connection to tubing (not shown) from a source of gas. Bifurcation connector 100 includes flexible tubular members 106 and 108 for connecting tubular members 101 and 103 to hollow stem members 86 and 88, respectively. Tubular members 106, 108 are preferably long enough to permit movement of bifurcation connection 100 towards and away from the patient's face when the tube assembly is in place.

Although flexible plastic may be used in all components of adapter 80, in a preferred embodiment of the present invention, branch portions 82, 84 of the Y-shaped member and hollow stem members 86, 88 are made of a rigid transparent plastic.

In a preferred embodiment of the present invention, radiopaque material is incorporated into substantially the entire length of tube 22.

The foregoing description is intended to illustrate and not to limit the present invention. Although only one embodiment has been described, other embodiments and variations may occur to those skilled in the art. It should accordingly be understood that the present invention should be limited only in accordance with the claims appended hereto.

What is claimed is:

1. A surgical device for conducting a gas between a patient's mouth and lungs comprising:
   a) an elongated flexible tubular member adapted to extend within said patient's respiratory system and having a proximal end portion for positioning at a patient's mouth and a distal end portion for positioning in a bronchus of a patient's lungs, said distal end portion having first and second orifices and said tubular member having first and second lumens for conducting gas from said proximal end portion to said first and second orifices at said distal end portion;
   b) seal means at said distal end portion for directing said gas from said orifices into desired regions of the a patient's lungs;
   c) adapter means formed integrally with said flexible tubular member at said proximal end portion thereof for connecting said lumens with a source of said gas, said adapter means comprising a Y-shaped member having first and second hollow branch portions which have center lines which define a plane and which converge to meet said first and second lumens and, with said first and second lumens, form first and second gas passages which extend between said hollow branch portions and the orifices at the distal end portion of said flexible tubular member, and first and second hollow stem members in fluid communication with and intersecting said plane defined by the center lines of the first and second hollow branch portions at about a right angle, and adapted to extend upwardly in front of a patient's face, said hollow stem members being in fluid communication with said first and second passages;
   d) connection means for introducing said gas from a gas source into said hollow stem members; and,
   e) a flexible plastic member encasing said Y-shaped member and the junction of said hollow stem members and said Y-shaped member.

2. A surgical device according to claim 1 wherein said hollow branch portion of said Y-shaped member and said hollow stem members are formed from a rigid plastic.

3. A surgical device according to claim 1 wherein said connection means comprises a bifurcation connector including a manifold chamber for splitting a single stream of gas into two streams of gas, a gas feed inlet in fluid communication with said manifold chamber, first and second gas feed outlets in fluid communication with said manifold chamber, and first and second flexible tubular members secured to said first and second gas feed outlets and in fluid communication with said first and second hollow stem members.

4. A surgical device according to claim 3 wherein said manifold, gas feed inlet and gas feed outlet comprise an integral member formed of a rigid plastic.

5. A surgical device according to claim 1 wherein sid flexible plastic member has a Shore A durometer hardness from about 60 to about 80.

* * * * *